United States Patent
Hölscher et al.

(10) Patent No.: US 10,876,068 B2
(45) Date of Patent: Dec. 29, 2020

(54) 2,3,6-TRIMETHYLCYCLOHEXANOL AS A SCENTING AND/OR FLAVORING AGENT

(71) Applicant: SYMRISE AG, Holzminden (DE)

(72) Inventors: Bernd Hölscher, Halle (DE); Manfred Meier, Fürstenberg (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/493,404

(22) PCT Filed: Nov. 27, 2017

(86) PCT No.: PCT/EP2017/080536
§ 371 (c)(1),
(2) Date: Sep. 12, 2019

(87) PCT Pub. No.: WO2018/171917
PCT Pub. Date: Sep. 27, 2018

(65) Prior Publication Data
US 2020/0017798 A1    Jan. 16, 2020

(30) Foreign Application Priority Data

Mar. 21, 2017 (WO) ................ PCT/EP2017/056708

(51) Int. Cl.
| | | |
|---|---|---|
| *C11B 9/00* | (2006.01) | |
| *A61K 8/34* | (2006.01) | |
| *A23L 27/20* | (2016.01) | |
| *C11D 3/00* | (2006.01) | |
| *C11D 3/50* | (2006.01) | |
| *C11D 17/06* | (2006.01) | |
| *A61Q 11/00* | (2006.01) | |

(52) U.S. Cl.
CPC .......... *C11B 9/0034* (2013.01); *A23L 27/203* (2016.08); *A61K 8/34* (2013.01); *A61Q 11/00* (2013.01); *C11D 3/001* (2013.01); *C11D 3/50* (2013.01); *C11D 17/06* (2013.01); *A23V 2002/00* (2013.01)

(58) Field of Classification Search
None
See application file for complete search history.

(56) References Cited

FOREIGN PATENT DOCUMENTS

| | | | |
|---|---|---|---|
| DE | 2317000 A1 | 10/1973 | |
| DE | 3003518 A1 | 8/1980 | |
| EP | 2389922 A1 | 11/2011 | |
| GB | 1411785 A | * 10/1975 | ............. C07C 35/08 |
| JP | S5022548 B1 | 7/1975 | |

OTHER PUBLICATIONS

International Search Report and Written Opinion dated Jan. 11, 2018, for corresponding PCT Application No. PCT/EP2017/080536.
Database Caplus; Chemical Abstracts Service, Columbus, Ohio, US; "Alkylcyclohexanols", 1976 XP002772579.

* cited by examiner

*Primary Examiner* — Michael P Cohen
(74) *Attorney, Agent, or Firm* — Polsinelli PC

(57) ABSTRACT

The present invention primarily concerns the use of 2,3,6-trimethylcyclohexanol as a fragrance and/or flavoring. The invention also concerns new fragrance and/or flavoring compositions comprising 2,3,6-trimethylcyclohexanol and their use, perfumed and/or flavored articles comprising 2,3,6-trimethylcyclohexanol and various methods for imparting, modifying and/or enhancing certain scent and/or flavor notes.

18 Claims, No Drawings

2,3,6-TRIMETHYLCYCLOHEXANOL AS A SCENTING AND/OR FLAVORING AGENT

CROSS-REFERENCE TO RELATED APPLICATIONS

This application is a national stage application (under 35 U.S.C. § 371) of PCT/EP2017/080536, filed Nov. 27, 2017, which claims benefit of European PCT Application No. PCT/EP2017/056708, filed Mar. 21, 2017, which are incorporated herein by reference in their entireties.

The present invention primarily concerns the use of 2,3,6-trimethylcyclohexanol, i.e. a compound of formula (I) as described herein, as a fragrance and/or flavoring. The invention further concerns new fragrance and/or flavoring compositions comprising the compound of formula (I) as described herein, perfumed and/or flavored articles comprising the compound of formula (I) as described herein, and various methods for imparting, modifying and/or enhancing certain scent and/or flavor notes.

Further aspects and preferred embodiments of the present invention can be derived from the following descriptions, the appended examples and, in particular, the appended patent claims.

Despite a number of existing fragrances and/or flavorings, there is still a general need for new fragrances and/or flavorings in the perfume and flavoring industry. For example, there is a need for fragrances and/or flavorings that are capable (in fragrance and/or flavoring compositions) of producing a primary flavor note as well as other interesting notes and of expanding the possibilities of the perfumer or flavorist with their novel respectively unique olfactory properties. In particular, there is an interest in fragrances with scent notes that are able to combine harmoniously with floral and/or fruity fragrances. Preferably, the different olfactory aspects and notes should be superimposed in order to create an overall complex olfactory impression.

For the creation of novel compositions, there is a constant need for fragrances and/or flavorings with special sensory properties that can serve as a basis for the composition of novel perfumes or aromas with complex sensory character. Preferred fragrances and/or flavorings should have, in addition to a particular note, other notes and aspects that give them character and complexity.

The search for suitable substances that led to the present invention was complicated by the following circumstances:
- the mechanisms of odor perception are not sufficiently known;
- the connections between the special odor perception on the one hand and the chemical structure of the associated fragrance on the other hand have not been sufficiently researched;
- often, even minor changes in the structure of a known fragrance cause major changes in the sensory properties and affect the tolerance for the human organism.

The primary objective therefore was to identify fragrances and/or flavorings that have an interesting, preferably complex and unique sensory profile and are suitable for use as fragrances in e.g. perfumery or as flavorings in e.g. edible preparations.

Within the context of the present invention, particular attention was paid to substances which are able to exhibit or impart, modify and/or enhance one, more than one or all of the notes green, woody, animal, earthy, ambry, fruity, floral and leather note.

The substances searched for should enable the production of novel fragrance and/or flavoring compositions with special scent or flavor notes and aspects. Of advantage would be those substances which are particularly suitable for combination with other fragrances or flavorings which have a woody, animal, earthy and amber note.

In addition, fragrances and/or flavorings fulfilling this primary objective should in addition to their primary properties, i.e. olfactory or flavor properties, preferably have additional positive secondary properties, such as a high stability under certain application conditions, a high efficacy, a good adhesion, a high substantivity or olfactory and/or flavor enhancing properties (so-called booster or enhancer effect), and/or in combination with other fragrances and/or flavorings round off their naturalness, freshness, fullness, (radiant) power and/or radiance, so that remarkable sensory effects can be achieved.

In accordance with the invention, the primary objective is solved by using the compound of formula (I) (2,3,6-trimethylcyclohexanol, CAS No. 58210-03-0)

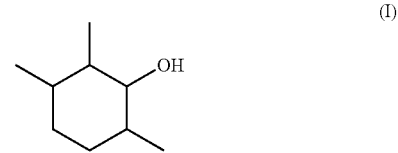

as a fragrance or flavoring.

The compound of formula (I) to be used according to the invention may be present as any stereoisomer and thus also in any optically active form. In the context of the present invention, any mixtures of stereoisomers of the compound of formula (I) can also be used, for example a mixture of diastereomers, a mixture of enantiomers or a racemate, i.e. the term "compound of formula (I)" in the context of this text also includes the said any mixtures of different stereoisomers of the compound of formula (I).

What is stated herein for a compound of formula (I), in particular the advantages described herein, also apply to a mixture of stereoisomers of the compound of formula (I) to be used in accordance with the invention (see above).

The compound of formula (I) has its own unique olfactory properties, which clearly stand out from and even exceed those of known fragrances and/or flavorings. The suitability of the compound of formula (I) as a fragrance and/or a flavoring was not known until now. It is therefore particularly surprising that a fragrance and/or flavoring with valuable, interesting and complex olfactory properties could be found in the field already well investigated.

Preferably, the use according to the invention concerns a use for imparting, modifying and/or enhancing one or more scent and/or flavor notes selected from the group consisting of the notes green, herbaceous, fresh, fruity, floral, woody, animal, sweet, earthy, ambry, greasy, metallic, balsamic and leather note, preferably one or more of the scent and/or flavor notes selected from the group consisting of the notes green, woody, animal, earthy, ambry, fruity, floral and leather note.

A preferred embodiment concerns the use of the compound of formula (I) for imparting one, two or more scent and/or flavor notes selected from the group consisting of the notes green, herbaceous, fresh, fruity, floral, woody, sweet, earthy, greasy, metallic and balsamic.

Another preferred embodiment concerns the use of the compound of formula (I) for imparting a green and/or fruity, preferably a green and fruity, preferably a pineapple-like, scent and/or flavor note and additionally one, two or more scent and/or flavor notes selected from the group consisting of the notes herbaceous, fresh, flowery, woody, sweet, earthy, fatty, metallic and balsamic.

The fact that the compound of formula (I) to be used according to the invention may impart a very complex and diverse olfactory and flavor impression, which otherwise can only be achieved by mixtures of several components (such as essential oils or spice mixtures), is particularly surprising.

In addition to the primary properties, namely olfactory and flavor properties, the compound of formula (I) also has positive secondary properties, in particular good adhesion and a high substantivity in comparison with fragrances with similar olfactory properties, as well as high stability in certain media and preparations and a high efficacy, and is also biodegradable.

The compound of formula (I) to be used in accordance with the invention has a high, very excellent stability, in particular in essentially neutral media, but in particular in alkaline and/or oxidizing media. In particular because of these properties, the compound of formula (I) is excellently suited for use as a fragrance and/or flavoring, in particular when it is used in perfumed or flavored articles (preparations) having a pH of 5.5 or greater, preferably greater than or equal to 6, preferably greater than or equal to 7, more preferably greater than or equal to 7.5, more preferably greater than or equal to 8; furthermore in oxidizing preparations preferably having a pH of greater than or equal to 7, preferably in oxidizing preparations having a pH of greater than or equal to 8. The indicated pH values refer to values measured at 25° C.

The compound of formula (I) to be used in accordance with the invention may advantageously increase the intensity of a mixture of fragrances or flavorings (composition of fragrances and/or flavorings) and round off the overall impression of the mixture in terms of odor and/or taste and may be used to confer more richness, freshness, (radiant) power, radiance, shine, roundness, harmony and/or naturalness to a composition of fragrances and/or flavorings.

Furthermore, the compound of formula (I) is suitable as an agent for increasing the substantivity and/or retention of a fragrance and/or flavoring mixture and/or as a fixator.

If, in the context of this text, a discrepancy should occur by mistake between the chemical name and the structural formula of the compound of formulae (I) presented, the structural formula presented shall apply.

Advantageously, the compound of formula (I) to be used in accordance with the invention also exhibits sensory properties of the ocimene species and has a chloroskatol note.

The chloroskatol note makes the compound of formula (I) suitable, among other things, as a signal substance in antibacterial applications.

Another preferred embodiment therefore concerns the use of the compound of formula (I) for imparting, modifying and/or enhancing one or more scent and/or flavor notes selected from the group consisting of the notes green, herbaceous, fresh, fruity, floral, woody, animalic, sweet, earthy, ambry, greasy, metallic, balsamic, leather note and chlorine note, preferably one or more of the scent and/or flavor notes selected from the group consisting of green, woody, animal, earthy, ambry, fruity, floral, leather and chlorine notes, more preferably the scent and/or flavor note chlorine.

In many countries, a chlorine-like scent and flavor note, especially a scent note, is associated with the impression of cleanliness, hygiene and antibacterial properties. For this reason, the use in accordance with the invention is particularly advantageous, since it can impart, modify and/or enhance a chlorine note without actually having to add chlorine to the fragrance and/or flavoring compositions or perfumed and/or flavored articles (as described below) containing the compound of formula (I) in accordance with the invention, or with having a much lower actual chlorine content which, without the odor enhancement by the compound of formula (I), would possibly not be sensorially detectable at all. This chlorine signaling effect of the compound of formula (I), i.e. giving the impression that a fragrance and/or flavoring composition in accordance with the invention or a perfumed and/or flavored article in accordance with the invention (as described below) is particularly clean, hygienic and/or antibacterial because of its sensory chlorine note or is particularly popular with many consumers and can be used advantageously in oral care products such as mouthwashes and dental care products, and surface cleaners such as toilet cleaners and all-purpose cleaners.

The compound of formula (I) is already known from literature (see e.g. WO2010122178, WO2014198602, WO2010097479, EP2389922, EP50229 and US20110294876). However, the state of the art does not describe the sensory properties and suitability as a fragrance and/or flavoring.

The compound of formula (I) to be used in accordance with the invention may be prepared by reactions and methods known per se. For example, the respective phenol (CAS No. 2416-94-6) or a corresponding ketone (e.g.: CAS No. 20030-30-2) can be hydrogenated to the compound of formula (I) with appropriate catalysts and conditions (the starting materials used are commercially available):

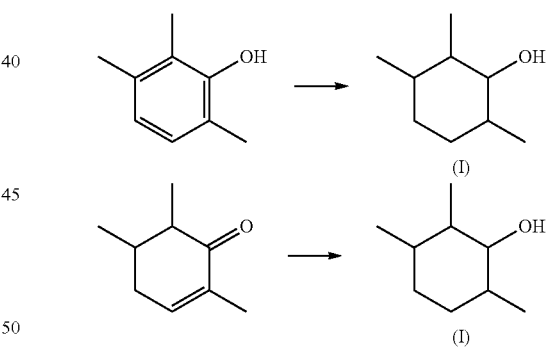

Production of the Compound of Formula (I) from the Respective Phenol (Above) or a Respective Ketone (Below) by Hydrogenation The compound of formula (I) to be used in accordance with the invention is normally used in a sensory effective amount, i.e. in a total amount in which it exerts a sensory effect. The compound of formula (I) to be used in accordance with the invention is preferably used together with other fragrances and/or flavorings. Such fragrance and/or flavoring compositions may be prepared in a customary manner, for example by simple mixing or homogenization of the components. These additional fragrances and/or flavorings may be any other fragrances and/or flavorings (preferred combinations can be derived from the following descriptions).

A further aspect of the present invention therefore concerns a fragrance and/or flavoring composition comprising or consisting of the compound of formula (I)

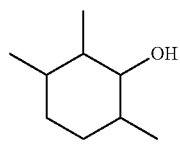

and one, two, three, four, five, six, seven, eight, nine, ten or more further fragrance(s) and/or flavoring(s), wherein the weight ratio of the total amount of the compound of formula (I) to the total amount of the further fragrance(s) and/or flavoring(s) is in the range from 1:1000 to 1:0.1, preferably from 1:1000 to 1:0.5.

In this context, it is preferred that the total amount of the compound of formula (I), based on the total weight of the fragrance and/or flavouring composition, is in the range of 0.0001 to 99.9% by weight, preferably 0.001 to 99.5% by weight, most preferably 0.01 to 99% by weight, 0.01 to 90% by weight, 0.05 to 80% by weight, 0.1 to 70% by weight, 0.25 to 50% by weight, 0.5 to 40% by weight or 0.75 to 25% by weight.

If the compound of formula (I) is mainly used to impart more freshness, radiation (radiance), rounding, harmony and/or naturalness to a fragrance and/or flavoring composition and/or to enhance certain notes (already present by further fragrances and/or flavorings), the total amount of the compound of formula (I) can also be relatively low and e.g. preferably in the range from 0.01 to 5 wt. %, more preferably in the range from 0.1 to 2 wt. %, based on the total amount of the fragrance and/or flavoring composition. If a comparatively low concentration is selected within the preferred concentration ranges, the inherent scent and/or taste notes indicated herein may not yet be imparted in individual cases, depending on the other components of the respective composition. Thus, depending on the desired effect of the compound of formula (I), a person skilled in the art can select an amount of compound of formula (I) which is suitable for the respective application.

Due to its olfactory properties, the compound of formula (I) is excellently suited for use in fragrance and/or flavoring compositions of the invention. The compound of formula (I) can be advantageously combined with a variety of other fragrances or flavorings and used in a wide variety of products and articles.

Preferably, for a fragrance and/or flavoring composition according to the invention, the total amount of the compound of formula (I) in the fragrance and/or flavoring composition is contained in a sensory effective amount, preferably in an amount sufficient to impart or enhance one or more scent and/or flavor notes selected from the group consisting of the notes green, herbaceous, fresh, fruity, flowery, woody, animalic, sweet, earthy, ambry, greasy, metallic, balsamic and leather note, preferably at least one of the scent and/or flavor notes selected from the group consisting of the notes green, woody, animalic, earthy, ambry, fruity, floral and leather note, preferably consisting of green and fruity, more preferably a leather note, and/or to modify one or more scent and/or flavor notes of a or the further fragrance(s) and/or flavoring(s) of the fragrance and/or flavoring composition in the direction of one or more of these scent and/or flavor notes.

It is further preferred for a fragrance and/or flavoring composition according to the invention that the total amount of the compound of formula (I) in the fragrance and/or flavoring composition is contained in a sensory effective amount, preferably in an amount sufficient to impart and/or enhance one or more scent and/or flavor notes selected from the group consisting of the notes green, herbaceous, fresh, fruity, flowery, woody, animalic, sweet, earthy, ambry, greasy, metallic, balsamic, leather note and chlorine note, preferably at least one of the scent and/or flavor notes selected from the group consisting of the notes green, woody, animalic, earthy, ambry, fruity, flowery, leather note and chlorine note, and/or to modify one or more scent and/or flavor notes of a respectively the further fragrance(s) and/or flavoring(s) of the fragrance and/or flavoring composition in the direction of one or more of said scent and/or flavor notes.

It is particularly preferred that
(i) the or one, more or all of the further fragrances and/or flavorings (also) impart, modify and/or enhance one or more scent and/or flavor notes selected from the group consisting of the notes green, herbaceous, fresh, fruity, floral, woody, animalic, sweet, earthy, ambry, greasy, metallic, balsamic and leather note, preferably one or more of the scent and/or flavor notes selected from the group consisting of the notes green, woody, animal, earthy, ambry, fruity, floral and leather note, particularly preferably selected from the group consisting of the notes fruity and floral, or
(ii) the or one, more or all of the further fragrances and/or flavorings impart, modify and/or enhance one or more scent and/or flavor notes other than those mentioned in (i).

It is further preferred that
(i) the or one, more or all of the further fragrances and/or flavorings (also) impart, modify and/or enhance one or more scent and/or flavor notes selected from the group consisting of the notes green, herbaceous, fresh, fruity, floral, woody, animalic, sweet, earthy, ambry, greasy, metallic, balsamic, leather note and chlorine note, preferably one or more of the scent and/or flavor notes selected from the group consisting of the notes green, woody, animal, earthy, ambry, fruity, flowery, leather note and chlorine note, particularly preferably selected from the group consisting of the notes fruity, flowery and chlorine note, or
(ii) the or one, more or all of the other fragrances and/or flavorings impart, modify and/or enhance one or more scent and/or flavor notes other than those mentioned in (i).

Examples of fragrances and/or flavorings which within the context of the present invention can be advantageously combined with the compound of formula (I) can be found, for example, in S. Arctander, Perfume and Flavor Materials, Vol. I and II, Montclair, N.J. 1969, Eigenverlag, or K. Bauer et al., Common Fragrance and Flavor Materials, 4th Edition, Wiley-VCH, Weinheim 2001.

The following are mentioned specifically: Extracts from natural raw materials such as essential oils, concretes, absolues, resins, resinoids, balsams, tinctures such as
ambratincture; amyris oil; angelica seed oil; angelica root oil; anise oil; valerian oil; basil oil; tree moss absolue; bay oil; mugwort oil; benzoeresin; bergamot oil; beeswax absolue; birch tar oil; bitter almond oil; savory oil; bucco leaf oil; cabreuva oil; cade oil; calmus oil; camphor oil; cananga oil; cardamom oil; cascarilla oil; cassia oil; cassie absolue; castoreum absolue; cedar leaf oil; cedar wood oil; cistus oil; citronella oil; lemon oil; copaiba balsam; copaiba balsam oil; coriander oil; costus root oil; cumin oil; cypress oil; davana oil; dill herb oil; dill seed oil; eau de brouts absolue; oakmoss absolue; elemi oil; tarragon oil; eucalyptus citriodora oil; eucalyptus oil; fennel oil; spruce needle oil; galbanum oil; galbanum resin; geranium oil; grapefruit oil; guaiac wood oil; gurujun balsam; gurujun balsam oil; helichrysum absolue; helichrysum oil; ginger oil; iris root absolue; iris root oil; jasmine absolue; calamus oil; camomile oil blue; camomile oil roman; carrot seed oil; cascarilla oil; pine needle oil; spearmint oil; caraway oil; labdanum oil; labdanum absolue; labdanum resin; lavandin absolue; lavandin oil; lavender absolue; lavender oil; lemongrass oil; lovage oil; distilled lime oil; pressed lime oil; linaloe oil; litsea cubeba oil; laurel leaf oil; macis oil; marjoram oil; mandarin oil; massoirind oil; mimosa absolue; musk seed oil; musk tincture; muscat sage oil; nutmeg oil; myrrh absolue; myrrh oil; myrtle oil; clove leaf oil; clove flower oil; neroli oil; olibanum absolue; olibanum oil; opopanax oil; orange blossom absolue; orange oil; origanum oil; palmarosa oil; patchouli oil; perilla oil; Peru balsam oil; parsley leaf oil; parsley seed oil; petitgrain oil; Peppermint oil; pepper oil; pimento oil; pine oil; poley oil; rose absolue; rosewood oil; rose oil; rosemary oil; sage oil dalmatian; sage oil Spanish; sandalwood oil; celery seed oil; spiked lavender oil; star anise oil; styrax oil; marigold oil; fir needle oil; tea-tree oil; turpentine oil; thyme oil; tolubalsam; tonka-absolue; tuberose absolue; vanilla extract; violet leaf absolue; verbena oil; vetiver oil; juniper berry oil; wine yeast oil; wormwood oil; wintergreen oil; ylang oil; hyssop oil; civet absolue; cinnamon leaf oil; cinnamon bark oil and fractions thereof, or components isolated therefrom;

single fragrances from the group of hydrocarbons such as 3-carene; α-pinene; β-pinene; α-terpinene; γ-terpinene; p-cymol; bisabols; camphene; caryophyllene; cedren; farnesene; limonene; longifolene; myrcene; ocimene; valence; (E,Z)-1,3,5-undecatriene; styrene; diphenylmethane;

aliphatic alcohols such as hexanol; octanol; 3-octanol; 2,6-dimethylheptanol; 2-methyl-2-heptanol; 2-methyl-2-octanol; (E)-2-hexenol; 1-octene-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals such as hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyloxyacetaldehyde; 1-(1-methoxy-propoxy)-(E/Z)-3-hexene;

aliphatic ketones and their oximes such as 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles such as 2-nonic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerianate; ethyl 2-methyl pentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl 3,7-dimethyl 2,6-octadiene oate; 4-methyl 2-pentyl crotonate; 4-methyl 2-pentyl crotonate; ethyl hexanoate; allyl hexanoate; ethyl heptanoate; ethyl heptanoate; allyl heptanoate; allyl heptanoate; methyl 2-nonate; methyl 2-nonate; allyl 2-isoamyloxy acetate; methyl 3,7-dimethyl 2,6-octadiene oate; 4-methyl 2-pentyl crotonate;

acyclic terpene alcohols such as geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-Dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

acyclic terpene aldehydes and ketones such as citronellal; 7-methoxy-3,7-dimethyloctanal; 2,6,10-trimethyl-9-undecenal; geranylacetone; and the dimethyl and diethyl acetals of geranial, neral;

cyclic terpene alcohols such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; as well as their formates, acetates, propionates, isobutyrates, butyrates, isovalerianates, pentanoates, hexanoates, crotonates, tiglinates and 3-methyl-2-butenoates; 3-methyl-2-butenoates, crotonates, tiglinates, and 3-methyl-2-butenoates;

cyclic terpene aldehydes and ketones such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethyl-ionone;

alpha-ionone; beta-damascenone; 1-(2,4,4-trimethyl-2-cyclohexen-1-yl)-2-buten-1-one; 1,3,4,6,7,8a-Hexahydro-1,1,5,5-tetramethyl-2H-2,4a-methano-naphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedrylketone);

cyclic alcohols such as 4-tert.-butylcyclohexanol; 3,3,5-trimethylcyclohexanol; 3-isocamphylcyclohexanol; 2,6,9-trimethyl-Z2,Z5, E9-cyclododecatri en-1-ol; 2-isobutyl-4-methyltetrahydro-2H-pyran-4-ol;

cycloaliphatic alcohols such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-Methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclo-hexyl)pentan-3-ol; 1-(2,2,6-trimethylcyclohexyl)hexan-3-ol;

cyclic and cycloaliphatic ethers such as cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydro-naphtho[2,1-b]furan; 3a-ethyl-6,6,9a-trimethyldodecahydronaphtho[2,1b]furan; 1,5,9-trimethyl-13- oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopenta-decenone; 3-methylcyclopenta-decanone; 4-(1-ethoxyvinyl)-3,3,5,5-tetramethylcyclohexanone; 4-tert.-Pentylcyclo-hexanone; 5-cyclohexadecen-1-one; 6,7-di hydro-1,1,2,3,3-pentamethyl-4(5H)-indanone; 8-cyclohexadecen-1-one; 9-cyclohepta-decen-1-one; cyclopentadecanone; cyclohexadecanone;

cycloaliphatic aldehydes such as 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

esters of cyclic alcohols such as 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclo-pentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5, or 6-indenyl acetate; 4,7-methano-3a,4,5,6,7,7a-hexahydro-5, or 6-indenyl propionate; 4,7-methano-3a,4,5,6,7,7a-hexa-hydro-5, or 6-indenyl isobutyrate; 4,7-methanooctahydro-5, or 6-indenyl acetate;

esters of cycloaliphatic alcohols such as 1-cyclohexylethylcrotonate;

esters of cycloaliphatic carboxylic acids such as allyl 3-cyclohexyl propionate; allyl cyclohexyloxy acetate; cis and trans methyl dihydroyasmonate; cis and trans methyl jasmonate; methyl 2-hexyl 3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

araliphatic alcohols such as benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-Dimethyl-3-phenylpropanol; 1-ethyl-1-methyl-3-phenylpropanol; 2-methyl-5-phenylpentanol; 3-methyl-5-phenylpentanol; 3-phenyl-2-propen-1-01; 4-methoxybenzyl alcohol; 1-(4-isopropylphenyl)ethanol;

esters of araliphatic alcohols and aliphatic carboxylic acids such as benzylacetate; benzyl propionate; benzyl isobutyrate; benzyl isovalerianate; 2-phenylethyl acetate; 2-phenylethyl propionate; 2-phenylethyl isobutyrate; 2-phenyl ethyl isovalerate; 1-phenylethyl acetate; alpha-trichloromethylbenzylacetate; alpha,alpha-dimethylphenylethyl acetate; alpha,alpha-dimethylphenylethylbutyrate; cinnamyl acetate; 2-phenoxyethylisobutyrate; 4-methoxybenzylacetate;

araliphatic ethers such as 2-phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; Phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert-butylphenyl)propanal; 3-(4-tert-butylphenyl)propanal; cinnamic aldehyde; alpha-butyl cinnamic aldehyde; alpha-hexyl cinnamic aldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as acetophenone; 4-methylacetophenone; 4-methoxyacetophenone; 4-tert.-butyl-2,6-dimethylaceto-phenone; 4-phenyl-2-butanone; 4-(4-hydroxyphenyl)-2-butanone; 1-(2-naphtha-lenyl)ethanone; 2-benzofuranylethanone; (3-methyl-2-benzofuranyl)ethanone; benzophenone; 1,1,2,3,3,6-hexamethyl-5-indanyl-methylketone; 6-tert-butyl-1,1-di-methyl-4-indanylmethylketone; 1-[2,3-di hydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

aromatic and araliphatic carboxylic acids and their esters such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allylphenoxyacetate; methyl salicylate; hexyl salicylate; cyclohexyl salicylate; cis-3-hexenyl salicylate; benzylsalicylate; phenylethyl salicylate; methyl 2,4-dihydroxy-3,6-dimethylbenzoate; ethyl-3-phenylglycidate; ethyl-3-methyl-3-phenylglycidate;

nitrogen-containing aromatic compounds such as 2,4,6-trinitro-1,3-dimethyl-5-tert.butylbenzene; 3,5-dinitro-2,6-dimethyl-4-tert.-butylacetophenone; cinnamic acid nitrile; 3-methyl-5-phenyl-2-pentenitrile; 3-methyl-5-phenylpentanoic acid nitrile; methylanthranilate; methy-N-methylanthranilate; Schiff's bases of methylanthranilate with 7-hydroxy-3,7-dimethyloctanal, 2-methyl-3-(4-tert.-butylphenyl)propanal or 2,4-dimethyl-3-cyclohexene carbaldehyde; 6-isopropyl quinoline; 6-isobutylquinoline; 6-sec.-butylquinoline; 2-(3-phenylpropyl)pyridine; indole; skatol; 2-methoxy-3-isopropylpyrazine; 2-isobutyl-3-methoxypyrazine;

phenols, phenylethers and phenyl esters such as estragole; anethole; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methyl phenol; 2-ethoxy-5-(1-propenyl)phenol; p-cresyl phenyl acetate;

heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadeca-nolide; 9-Hexadecene-1,16-olide; 10-oxa-1,16-hexadecanolide; 11-oxa-1,16-hexa-decanolide; 12-oxa- 1,16-hexadecanolide; ethylene-1,12-dodecandioate; ethylene-1,13-tridecandioate; 2,3-di hydrocoumarin; octahydrocoumarin.

In accordance with a preferred embodiment of the fragrance and/or flavoring composition of the invention, the compound of formula (I) to be used in accordance with the invention is preferably combined with one or more, particularly preferably two, three, four, five or more, floral and/or fruity further fragrances and/or flavorings.

Accordingly, the present invention also concerns a fragrance and/or flavoring composition comprising one, two, three, four, five or more (further) fragrances and/or flavorings which impart a floral and/or fruity scent and/or flavor.

In this case, the compound of formula (I) to be used in accordance with the invention advantageously (at least partially) enhances the scent and/or flavor of the floral and/or fruity note(s).

Floral fragrances and/or flavorings with which the compound of formula (I) to be used according to the invention (in particular in fragrance and/or flavoring compositions of the invention) can be advantageously combined are preferably selected from the group consisting of:

Hydroxycitronellal, methoxycitronellal, cyclamenaldehyde [2-methyl-3-(4-isopropylphenyl)propanal], 1-(4-isopropyl-cyclohexyl)ethanol (Mugetanol®), 4-tert.-butyl-α-methyldihydrocinnamic taldehyde (Lilial®), cis-hexahydrocuminyl alcohol (Mayol®), 3-[4-(1,1-dimethylethyl)phenyl]propanal (Bourgeonal®), 2,2-dimethyl-3-(3-methylphenyl)-propanol (Majantol®), 3-methyl-3-(3-methylbenzyl)-butan-2-ol, 2-isobutyl-4-methyltetra-hydro-2H-pyran-4-ol (Florosal, 2-methyl-3-(3, 4-methylenedioxyphenyl)propanal (Heliofolal®), 4-(4-hydroxy-4-methylpentyl)-3-cyclohexene carbaldehyde (Lyral®), 4-(octahydro-4,7-methano-5H-inden-5-ylidene-butanal (Dupical®), vernaldehyde, 4-(4-methyl-3-penten-1-yl)-3-cyclohexene carbaldehyde (Vertomugal®), octahydro-5-(4-methoxybutyl idene)-4,7-methano-1H-indene (Mugoflor®), 2,6-dimethyl-2-heptanol (Freesiol®), 1-ethyl-1-methyl-3-phenylpropanol (Phemec®), 2,2-dimethyl-3-phenyl-1-propanol (Muguet alcohol), profarnesol, dihydrofarnesol, farnesol, nerolidol, hydroxycitronellaldimethylacetal, hexylbenzoate, geraniol, nerol, linalool, tetrahydrogeraniol, tetrahydrolinalool, ethyllinalool, geranyltiglinate, phenethyl alcohol (2-phenylethyl alcohol), citronellol, rose oxide, 2-methyl-5-phenylpentanol (rosaphene), 3-methyl-5-phenylpentanol (phenoxanol), methyldihydrojasmonate (Hedion®, Hedione® high cis), 2-heptylcyclopentanone (Projasmon P), cis-jasmon, dihydrojasmon, Cinnamon alcohol (3-phenyl-2-propen-1-01), dihydrocinnamon alcohol (3-phenylpropanol), 2-methyl-4-phenyl-1,3-dioxolane (Jacinthaflor@) and dihydromyrcenol (2,6-dimethyl-7-octen-2-ol).

Fruity fragrances and/or flavorings with which the compound of formula (I) to be used according to the invention can be advantageously combined, and which are therefore particularly preferred (further) fragrances and/or flavorings of a fragrance and/or flavoring composition of the invention, are preferably selected from the group consisting of:

2-methyl-butyric acid ethyl ester, 4-(p-hydroxyphenyl)-2-butanone, ethyl-3-methyl-3-phenylglycidate, butyric acid isoamyl ester, acetic acid isoamyl ester, acetic acid n-butyl ester, butyric acid ethyl ester, 3-methyl-butyric acid ethyl ester, n-hexanoic acid ethyl ester, n-hexanoic acid allyl ester, Ethyl-2-trans-4-cis-decadienoate, 1,1-dimethoxy-2,2,5-trimethyl-4-hexane, 2,6-dimethyl-5-hepten-1-al, gamma-undecalactone, gamma-nonalactone, hexanal, 3Z-hexenal, n-decanal, n-dodecanal, citral, vanillin, ethylvanillin, maltol, ethylmaltol and mixtures thereof.

Fragrance and/or flavoring compositions of the invention which contain the compound of formula (I) can be in liquid form, undiluted or diluted with a solvent or are advantageously used for perfuming or flavoring. Preferred solvents for this purpose are ethanol, isopropanol, diethylene glycol monoethyl ether, glycerol, propylene glycol, 1,2-butylene glycol, dipropylene glycol, diethyl phthalate, triethyl citrate, isopropyl myristate, triacetine and diacetine.

Furthermore, fragrance and/or flavoring compositions of the invention may be adsorbed on a carrier which provides both a fine distribution of the fragrance and/or flavoring in the product and a controlled release during application. Such carriers may be porous inorganic materials such as light sulphate, silica gels, zeolites, gypsums, clays, clay granules, gas concrete, etc. or organic materials such as wood, cellulose-based materials, sugar, dextrins (e.g. maltodextrin) or plastics such as PVC, polyvinyl acetates or polyurethanes. The combination of a composition according to the invention and a carrier is also to be understood as a fragrance and/or flavoring composition of the invention or may be presented as an article according to the invention (as described below).

Fragrance and/or flavoring compositions or articles of the invention (as described below) may also be microencapsulated, spray-dried, or may be provided as inclusion complexes or as extrusion products and, in the case of a fragrance and/or flavoring composition, may be added in this form e.g. to an article to be perfumed or flavored (as described below).

If necessary, the properties of such modified compositions or articles can be further optimized by so-called "coating" with suitable materials with a view to a more targeted release of fragrance, preferably using wax-like plastics such as polyvinyl alcohol. The resulting products in turn represent articles of the invention.

Microencapsulation can, for example, be achieved by the so-called coacervation method using capsule materials such as polyurethane-like substances or soft gelatin.

Spray-dried products are preferably produced by spray-drying an emulsion or dispersion containing the fragrance and/or flavoring composition, whereby modified starches, proteins, dextrin and vegetable gums can be used as carriers.

Inclusion complexes can be produced e.g. by incorporating dispersions of the fragrance and/or flavoring composition and cyclodextrins or urea derivatives into a suitable solvent, e.g. water.

Extrusion products can be obtained, e.g., by using the fragrance and/or flavoring compositions with a suitable waxy substance and by extrusion followed by solidification, if necessary, in a suitable solvent, e.g. isopropanol.

A further aspect of the present invention concerns the use of a fragrance and/or flavoring composition of the invention to impart, modify and/or enhance one or more scents and/or flavor selected from the group consisting of the notes green, herbaceous, fresh, fruity, flowery, woody, animalic, sweet, earthy, ambry greasy, metallic, balsamic and leather note, preferably at least one of the scent and/or flavor notes selected from the group consisting of the notes green, woody, animalic, earthy, ambry, fruity, floral and leather note.

Also preferred is the use of a fragrance and/or flavoring composition of the invention for imparting, modifying and/or enhancing one or more scent and/or flavor notes selected from the group consisting of the notes green, herbaceous, fresh, fruity, flowery, woody, animal, sweet, earthy, ambry, greasy, metallic, balsamic, leather note and chlorine note, preferably at least one of the scent and/or flavor notes selected from the group consisting of green, woody, animal, earthy, ambry, fruity, flowery, leather note and chlorine note.

For preferred embodiments, the above mentioned in connection with the use according to the invention or a fragrance and/or flavoring composition according to the invention shall apply mutatis mutandis.

Fragrance and/or flavoring compositions of the invention may advantageously be used in concentrated form, in solutions or in modified form as described above for the production of perfumed and/or flavored articles of the invention (as described herein below) such as perfume extracts, eau de parfums, eau de toilettes, shaving lotions, eau de colognes, pre-shave products, splash colognes and perfumed refreshing wipes, as well as the perfuming of acidic, alkaline and neutral detergents, such as floor cleaners, window glass cleaners, dishwashing detergents, bathroom and sanitary cleaners, scouring milk, solid and liquid WC cleaners, powder and foam carpet cleaners, textile fresheners, ironing aids, liquid laundry detergents, powder laundry detergents, laundry pretreatment agents such as bleaching agents, soaking agents and stain removers, fabric softeners, washing soaps, washing tablets, disinfectants, surface disinfectants and air fresheners in liquid, gel or solid form, aerosol sprays, waxes and polishes such as furniture polishes, floor waxes, shoe polishes and body care products such as solid and liquid soaps, shower gels, shampoos, shaving soaps, shaving foams, bath oils, cosmetic emulsions of oil-in-water, water-in-oil and water-in-oil-in-water types such as skin creams and lotions, facial creams and lotions, sun protection creams and lotions, after-sun creams and lotions, hand creams and lotions, foot creams and lotions, depilatory creams and lotions, after-shave creams and lotions, tanning creams and lotions, hair care products such as hair sprays, hair gels, hair lotions, hair conditioners, permanent and semi-permanent hair dyes, hair deformers such as cold waves and hair straighteners, hair toners, hair creams and lotions, deodorants and antiperspirants such as underarm sprays, roll-ons, deodorant sticks, deodorant creams, decorative cosmetic products such as eye shadows, nail varnishes, make-ups, lipsticks, mascara as well as candles, lamp oils, incense sticks, insecticides, repellents and fuels.

Another aspect of the present invention concerns a method for imparting, enhancing and/or modifying one or more scent and/or flavor notes selected from the group consisting of the notes green, herbaceous, fresh, fruity, floral, woody, animal, sweet, earthy, ambry, greasy, metallic, balsamic and leather note, preferably for imparting, enhancing and/or modifying one or more scent and/or flavor notes selected from the group consisting of the notes green, woody, animalic, earthy, ambry, fruity, floral and leather note, comprising or consisting of the following steps:

(a) Providing
    (a.1) the compound of formula (I)

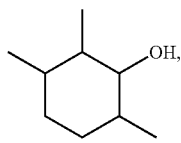

and
(a.2) one, two, three, four, five, six, seven, eight, nine, ten or more further fragrance(s) and/or flavoring(s) with one or more scent and/or flavor note(s) selected from the group consisting of the notes green, herbaceous, fresh, fruity, floral, woody, animal, sweet, earthy, ambry, greasy, metallic, balsamic and leather note, preferably with one or more scent and/or flavor note(s) selected from the group consisting of the notes green, woody, animal, earthy, ambry, fruity, floral and leather note, (b) Adding the compound of formula (I) (a.1) to the other fragrance(s) and/or flavoring(s) (a.2), in a sensory effective amount, preferably in an amount sufficient to impart, enhance and/or modify one or more scent and/or flavor notes selected from the group consisting of the notes green, herbaceous, fresh, fruity, floral, woody, animalic, sweet, earthy, ambry, greasy, metallic, balsamic and leather note, preferably in an amount sufficient to impart, modify and/or enhance one or more scent and/or flavor notes selected from the group consisting of the notes green, woody, animal, earthy, ambry, fruity, floral and leather note.

Also preferred is a method for imparting, enhancing and/or modifying one or more scent and/or flavor notes selected from the group consisting of green, herbaceous, fresh, fruity, floral, woody, animal, sweet, earthy, ambry, greasy, metallic, balsamic, leather note and chlorine note, preferably for imparting, enhancing and/or modifying one or more scent and/or flavor notes selected from the group consisting of the notes green, woody, animalic, earthy, ambry, fruity, floral, leather note and chlorine note, comprising or consisting of the following steps:

(a) Providing
    (a.1) the compound of formula (I)

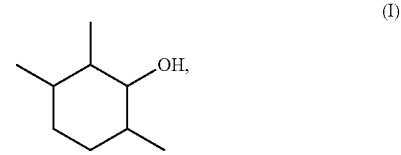

and
(a.2) one, two, three, four, five, six, seven, eight, nine, ten or more further fragrance(s) and/or flavoring(s) with one or more scent and/or flavor note(s) selected from the group consisting of the notes green, herbaceous, fresh, fruity, floral, woody, animalic, sweet, earthy, ambry, greasy, metallic, balsamic, leather note and chlorine note, preferably with one or more scent and/or flavor notes selected from the group consisting of green, woody, animalic, earthy, ambry, fruity, floral, leather note and chlorine note, (b) Adding the compound of formula (I) (a.1) to the other fragrance(s) and/or flavoring(s) (a.2) in a sensory effective amount, preferably in an amount sufficient to impart, enhance and/or modify one or more scent and/or flavor notes selected from the group consisting of the notes green, herbaceous, fresh, fruity, floral, woody, animalic, sweet, earthy, ambry, greasy, metallic, balsamic, leather note and chlorine note, preferably in an amount sufficient to impart, modify and/or enhance one or more scent and/or flavor notes selected from the group consisting of the notes green, woody, animalic, earthy, ambry, fruity, floral, leather note and chlorine note.

The finding that the compound of formula (I) can function excellently as a so-called booster (enhancer) stands also in connection with the method described herein and its use for imparting, modifying and/or enhancing a scent and/or flavor note.

A preferred embodiment thus concerns a method according to the invention for modifying and/or boosting a scent and/or flavor, in particular with one, more or all of the notes floral, fruity and/or woody, comprising or consisting of the following steps:
(a) Providing
 (a.1) the compound of formula (I)

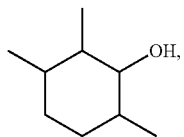

(I)

and
 (a.2) one or more further fragrances and/or flavorings having one or more of the scent and/or flavor notes selected from the group consisting of floral, fruity and/or woody,
(b) adding the compound of formula (I) (a.1) to the further fragrances and/or flavorings (a.2) in a sensory effective amount, preferably in an amount sufficient to sensory modify and/or enhance the scent and/or flavor impression of the further fragrances and/or flavorings (a.2).

A further aspect of the present invention concerns a perfumed and/or flavored article comprising or consisting of
(i) a fragrance and/or flavoring composition according to the invention (as described herein),
or
the compound of formula (I)

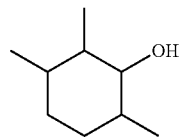

(I)

and one, two, three, four, five, six, seven, eight, nine, ten or more further fragrance(s) and/or flavoring(s), wherein the weight ratio of the total amount of the compound of formula (I) to the total amount of further fragrance(s) and/or flavoring(s) is in the range from 1:1000 to 1:0.1, preferably from 1:1000 to 1:0.5,
and
(ii) one or more further component(s), preferably at least one or more, preferably one, two, three, four, five or more, additive(s), excipient(s) and/or active substance(s).

With respect to preferred embodiments, the above mentioned in connection with a use in accordance with the invention, a fragrance and/or flavoring composition in accordance with the invention or a method in accordance with the invention shall apply mutatis mutandis.

Preferably, an article according to the invention is selected from the group consisting of laundry and cleaning agents, hygiene or care products, preferably in the field of body and hair care, cosmetics and household, preferably from the group consisting of perfume extracts, eau de parfums, eau de toilettes, shaving lotions, eau de colognes, pre-shave products, splash colognes, perfumed refreshing wipes, acidic, alkaline or neutral detergents, textile fresheners, ironing aids, liquid laundry detergents, powder laundry detergents, laundry pretreatments, fabric softeners, washing soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

An article according to the invention is further preferably selected from the group consisting of laundry detergents and cleaning agents, hygiene or care products, preferably in the field of body, hair and oral care, cosmetics and household, preferably from the group consisting of surface cleaners, WC cleaners, all-purpose cleaners, mouthwashes, toothpastes, tooth gels, toothpastes, tooth powders, tooth care chewing gums, perfume extracts, eau de parfums, eau de toilettes, shaving lotions, eau de colognes, pre-shave products, splash colognes, perfumed refreshing wipes, acidic, alkaline or neutral detergents, textile fresheners, ironing aids, liquid laundry detergents, powder laundry detergents, laundry pretreatment agents, fabric softeners, washing soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants, antiperspirants, decorative cosmetic products, candles, lamp oils, incense sticks, insecticides, repellents and fuels.

In addition, a perfumed and/or flavored article according to the invention is considered to be preferred, wherein
 component (i) is contained in a sensory effective amount, preferably in an amount sufficient for a consumer to perceive one or more scent and/or flavor notes selected from the group consisting of the notes green, herbaceous, fresh, fruity, flowery, woody, animal, sweet, earthy, ambry, greasy, metallic, balsamic and leather note, preferably one or more scent and/or flavor notes selected from the group consisting of the notes green, woody, animal, earthy, ambry, fruity, floral and leather note,
 and/or
 one, two, three, four, five, six, seven, eight, nine, ten or more of the other fragrances and/or flavorings in component (i) impart, modify and/or enhance a green, woody, animal, earthy, ambry, fruity, floral and/or leather scent and/or flavor.

It is particularly preferred for a perfumed and/or flavored article according to the invention
 that component (i) is contained in a sensory effective amount, preferably in an amount sufficient for a consumer to perceive one or more scent and/or taste notes selected from the group consisting of the notes green, herbaceous, fresh, fruity, floral, woody, animalic, sweet, earthy, ambry, greasy, metallic, balsamic, leather note and chlorine note, preferably one or more scent and/or flavor notes selected from the group consisting of green, woody, animal, earthy, ambry, fruity, floral, leather note and chlorine note,
 and/or
 that one, two, three, four, five, six, seven, eight, nine, ten or more of the other fragrances and/or flavorings in component (i) impart, modify and/or enhance a green, woody, animal, earthy, ambry, fruity, flowery, leathery and/or chlorine-like scent and/or flavor.

It is also preferred that the perfumed and/or flavored article contains a total amount of compound of formula (I), based on the total weight of the article, ranging from 0.00001 to 10% by weight, preferably from 0.0001 to 5% by weight, particularly preferably from 0.001 to 2% by weight, more preferably from 0.005 to 1% by weight.

The additives, adjuvants and/or active ingredients described above are preferably not fragrances and/or flavorings and, if present, are preferably selected from the group consisting of:

Preservatives, preferably those mentioned in US 2006/0089413, abrasives, antiacne agents and sebum reducing agents, preferably those mentioned in WO 2008/046791, anti-aging agents, preferably those mentioned in WO 2005/123101, antibacterial agents, anti-cellulite agents, anti-dandruff agents, preferably those mentioned in WO 2008/046795, anti-inflammatory agents, irritation inhibiting agents, anti-irritants (anti-inflammatory, irritant inhibiting and anti-irritant agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carrier materials, preferably those mentioned in WO 2005/123101, Chelating agents, preferably those mentioned in WO 2005/123101, cell stimulants, cleansing agents, caring agents, depilatories, surfactants, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film formers, (further) fixing agents, foaming agents, foam stabilizers, substances for preventing foaming, foam boosters, fungicides, gelling agents and gel-forming agents, preferably those mentioned in WO 2005/123101, hair care products, hair deforming agents, hair straightening agents, moisture regulators (moisturizing, moistening and/or moisture retaining substances), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removing agents, optical brightening agents, impregnating agents, dirt repellents, friction reducing agents, lubricants, moisturizing creams, ointments, opacifiers, plasticizers, opacifiers, polishes, brighteners, polymers, preferably those mentioned in WO 2008/046676, powders, proteins and protein hydrolysates, preferably those mentioned in WO 2005/123101 and WO 2008/046676, re-fattening agents, abrasive agents, skin soothing agents, skin cleansing agents, skin caring agents, skin repair agents, preferably containing cholesterol and/or fatty acids and/or ceramides and/or pseudoceramides, preferably those mentioned in WO 2006/053912, skin whitening agents, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV absorbing agents and UV filters, preferably those mentioned in WO 2005/123101, benzylidene beta-dicarbonyl compounds, preferably those mentioned in WO 2005/107692, alpha-benzoyl cinnamic acid nitriles, preferably those mentioned in WO 2006/015954, AhR receptor antagonists, preferably those mentioned in WO 2007/128723 and WO 2007/060256, laundry detergents, fabric softeners, suspending agents, skin tanning agents, preferably those mentioned in WO 2006/045760, thickeners, vitamins, preferably those mentioned in WO 2005/123101, fatty oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids), polyhydroxy fatty acids), preferably those mentioned in WO 2005/123101, dyes and color protecting agents as well as pigments, preferably those mentioned in WO 2005/123101, anticorrosives, alcohols and polyols, preferably those mentioned in WO 2005/123101, surfactants, preferably those mentioned in WO 2005/123101, animal extracts, yeast extracts, Extracts of algae or microalgae, electrolytes, liquefiers, organic solvents, preferably those mentioned in WO 2005/123101, hair growth modulating agents (hair growth promoting or hair growth inhibiting), preferably those mentioned in EP 2168570 and EP 2193785 or silicones and silicone derivatives, preferably those mentioned in WO 2008/046676, preferably from the group consisting of preservatives, inorganic salts, chelating agents, surfactants, skin and/or hair care agents, enzymes, emulsifiers, fats, fatty oils, waxes, fatty alcohols, silicones, silicone derivatives and water.

According to a preferred embodiment, the perfumed and/or flavored article according to the invention, as described above, is a preparation (according to the invention) for nutrition, oral hygiene or pleasure.

Preparations serving the purpose of nutrition or pleasure include, for example, bakery products (e.g. bread, dry biscuits, cakes, other pastries), confectionery (e.g. chocolates, chocolate bar products, other bar products, fruit gums, hard and soft caramels, chewing gum), alcoholic or non-alcoholic beverages (e.g. coffee, tea, wine, beverages containing wine, beer, beverages containing beer, liqueurs, spirits, brandies, lemonades containing fruit, isotonic beverages, soft drinks, nectars, fruit and vegetable juices, fruit or vegetable juice preparations), instant beverages (e.g. instant cocoa drinks, instant tea drinks, instant coffee drinks), meat products (e.g. ham, fresh sausage or raw sausage preparations, seasoned or marinated fresh or salted meat products), eggs or egg products (dried egg, egg white, egg yolk), cereal products (e.g. breakfast cereals, muesli bars, pre-cooked ready-made rice products), dairy products (e.g. milk drinks, milk ice cream, yoghurt, kefir, cream cheese, soft cheese, hard cheese, dried milk powder, whey, butter, buttermilk, partially or completely hydrolyzed products containing milk protein), products made from soy protein or other soybean fractions (e.g. soy milk and products made from it, preparations containing soy lecithin, fermented products such as tofu or tempe or products made from them, soy sauces), fruit preparations (e.g. jams, fruit ice cream, fruit sauces, fruit fillings), vegetable preparations (e.g. Ketchup, sauces, dried vegetables, frozen vegetables, pre-cooked vegetables, pickled vegetables, cooked vegetables), snacks (e.g. baked or deep-fried potato chips or potato dough products, bread dough products, corn or peanut-based extrudates), fat and oil-based products or emulsions thereof (e.g. Mayonnaise, remoulade, dressings, seasoning preparations), other ready meals and soups (e.g. dry soups, instant soups, pre-cooked soups), spices, seasoning mixtures and in particular seasonings, which are used for example in the snack sector.

Preparations according to invention can be present e.g. as semi-finished product or as seasoning mixture.

Preparations according to the invention may in particular serve as semi-finished goods for the production of further preparations serving the purpose of nutrition or pleasure (also according to the invention), in particular in spray-dried form. Preparations according to the invention may also be presented in the form of capsules, tablets (uncoated and coated tablets, e.g. enteric coatings), dragées, granules, pellets, solid mixtures, dispersions in liquid phases, emulsions, powders, solutions, pastes or other preparations which can be swallowed or chewed as food supplements.

Preparations in accordance with the invention which serve the purpose of oral hygiene are in particular oral and/or dental hygiene products such as toothpastes, tooth gels, tooth powder, mouthwashes, chewing gums and other oral hygiene products.

Further common active substances, basic substances, auxiliaries and additives for preparations serving the purpose of nutrition, oral hygiene or pleasure may be contained in amounts of 5 to 99.9999% by weight, preferably 10 to 80% by weight, based on the total weight of the preparation. In addition, the preparations may contain water in an amount of up to 99.9% by weight, preferably 5 to 80% by weight, based on the total weight of the preparation.

Preparations according to the invention (as examples of articles according to the invention) are prepared according to a preferred embodiment by incorporating compounds as a substance, as a solution (e.g. in ethanol, water or 1,2-propylene glycol) or in the form of a mixture with a solid or liquid carrier (e.g. maltodextrin, starch, silica gel), other aromas or flavorings and, where appropriate, other auxiliaries and/or stabilizers (e.g. natural or artificial polysaccharides and/or plant gums such as modified starches or gum arabic) into a basic preparation serving the purpose of nutrition, oral hygiene or pleasure. Advantageously, preparations according to the invention in the form of a solution and/or suspension or emulsion may also be converted into a solid preparation according to the invention (preferably semi-finished product) by spray drying.

The spray-dried solid preparations in accordance with the invention (as a further example of an article in accordance with the invention) are particularly suitable as semi-finished products for the production of further preparations in accordance with the invention. The spray-dried solid preparations according to the invention preferably contain 50 to 95% by weight of carriers, in particular maltodextrin and/or starch, 5 to 40% by weight of excipients, preferably natural or artificial polysaccharides and/or plant gums such as modified starches or gum arabic.

According to another preferred embodiment, the compound of formula (I) and, where appropriate, other components of the preparation in accordance with the invention, are first incorporated in emulsions, in liposomes, e.g. starting from phosphatidylcholine, in microspheres, in nanospheres or also in capsules, granules or extrudates of a matrix suitable for foodstuffs and luxury foods, e.g. from starch, starch derivatives (e.g. modified starch), cellulose or cellulose derivatives (e.g. hydroxypropyl cellulose), other polysaccharides (e.g. dextrin, alginate, curdlan, carrageenan, chitin, chitosan, pullulan), natural fats, natural waxes (e.g. beeswax, carnauba wax), from proteins, e.g. gelatin or other natural products (e.g. shellac). Depending on the matrix, the products can be obtained by spray drying, spray granulation, melt granulation, coacervation, coagulation, extrusion, melt extrusion, emulsion processes, coating or other suitable encapsulation emthods and, if necessary, a suitable combination of the above-mentioned methods. In another preferred method of producing a preparation in accordance with the invention, compounds are first complexed with one or more complexing agents, for example with cyclodextrins or cyclodextrin derivatives, preferably α- or β cyclodextrin, and used in this complexed form.

A preparation according to the invention is particularly preferred, wherein the matrix is selected in such a way that the compound of formula (I) is slow-released from the matrix, so that a long-lasting effect is achieved. A fat, wax, polysaccharide or protein matrix is particularly preferred in this respect.

As further components of preparations according to the invention, serving the purpose of nutrition or pleasure, may be used common basic, auxiliary and additive substances for foodstuffs or luxury foods, e.g. water, mixtures of fresh or processed, vegetable or animal basic or raw materials (e.g. raw, roasted, dried, fermented, smoked and/or cooked meat, bones, cartilage, fish, vegetables, fruits, herbs, nuts, vegetable or fruit juices or pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hydrogenated fats (e.g. tallow, lard, palm fat, coconut fat, hydrogenated vegetable fat), oils (e.g. sunflower oil, peanut oil, corn oil, olive oil, fish oil, soybean oil, sesame oil), fatty acids or their salts (e.g. potassium stearate), proteinogenic or non-proteinogenic amino acids and related compounds (e.g. γ-aminobutyric acid, taurine), peptides (e.g. glutathione), native or processed proteins (e.g. gelatin), enzymes (e.g. peptidases), nucleic acids, nucleotides, taste correctives for unpleasant taste impressions, further taste modulators for other, usually not unpleasant taste impressions, other taste modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidifiers (e.g. malic acid, acetic acid, citric acid, tartaric acid, phosphoric acid), bitter substances (e.g. quinine, caffeine, limonine, amarogentin, humolones, lupolones, catechins, tannins), mineral salts (e.g. sodium chloride, potassium chloride, magnesium chloride, sodium phosphates), enzymatic browning inhibitors (e.g. sulfit, ascorbic acid), essential oils, plant extracts, natural or synthetic dyes or color pigments (e.g. carotenoids, flavonoids, anthocyanins, chlorophyll and their derivatives), spices, trigeminal active substances or plant extracts containing such trigeminal active substances, synthetic, natural or nature-identical flavorings or fragrances as well as odor correcting agents.

Dental care products (as a base for preparation according to the invention serving oral care) usually comprise an abrasive system (abrasive or polishing agent) such as silicas, calcium carbonates, calcium phosphates, aluminum oxides and/or hydroxyapatites, surface active substances such as sodium lauryl sulfate, sodium lauryl sarcosinate and/or cocamidopropyl betaine, humectants such as glycerin and/or sorbitol, thickeners such as carboxymethylcellulose, polyethylene glycols, carrageenan and/or Laponite®, sweeteners such as saccharin, taste correctives for unpleasant taste impressions, taste correctives for other, generally not unpleasant taste impressions, taste modulating substances (e.g. inositol phosphate, nucleotides such as guanosine monophosphate, adenosine monophosphate or other substances such as sodium glutamate or 2-phenoxypropionic acid), cooling agents such as menthol, menthol derivatives (e.g. L-menthol, L-menthyl lactate, L-menthyl alkyl carbonates, menthone ketals, menthanecarboxylic acid amides), 2,2,2-trialkyacetic acid amides (e.g. 2,2-diisopropylpropionic acid methylamide), icilin and icilin derivatives, stabilizers and active ingredients, such as sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavors and/or sodium bicarbonate or odor correctives.

Chewing gums (as another example of preparations according to the invention serving the purpose of oral hygiene) usually include a chewing gum base, i.e. a chewing gum mass which becomes plastic when chewed, various types of sugar, sugar substitutes, other sweet-tasting substances, sugar alcohols, taste correctives for unpleasant taste impressions, other taste modulators for further, usually not unpleasant taste impressions, taste modulating substances (e.g. inositol phosphate, nucleotides such as guanosine monophosphate, adenosine monophosphate or other substances such as sodium glutamate or 2-phenoxypropionic acid), humectants, thickeners, emulsifiers, flavors and stabilizers or odor correctives.

Another aspect of the present invention concerns a method for perfuming and/or flavoring an article, comprising or consisting of the following steps:
(a) Providing
  (a.1) fragrance and/or flavoring composition (as described herein),
  or
  (a.2) the compound of formula (I)

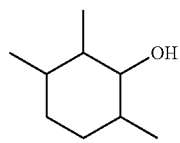

(I)

and optionally one, two, three, four, five, six, seven, eight, nine, ten or more further fragrance(s) and/or flavoring(s), wherein the weight ratio of the total amount of the compound of formula (I) to the total amount of further fragrance(s) and/or flavoring(s) is in the range from 1:1000 to 1:0.1, preferably from 1:1000 to 1:0.5,
and
(b) Adding the fragrance and/or flavoring composition (a.1) or the compound/fragrances (a.2).) to the article to be perfumed and/or flavored, in a sensory effective amount, preferably in an amount sufficient to impart, enhance and/or modify one or more scent and/or taste notes selected from the group consisting of the notes green, herbaceous, fresh, fruity, floral, woody, animalic, sweet, earthy, ambry, greasy, metallic, balsamic and leather note, preferably one or more of the scent and/or flavor notes selected from the group consisting of the notes green, woody, animalic, earthy, ambry, fruity, floral and leather note.

Preferred is a method in accordance with the invention for perfuming and/or flavoring an article, comprising or consisting of the following steps:
(a) Providing
  (a.1) a fragrance and/or flavoring composition (as described herein),
  or
  (a.2) the compound of formula (I)

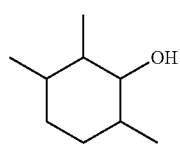

(I)

and optionally one, two, three, four, five, six, seven, eight, nine, ten or more further fragrance(s) and/or flavoring(s), wherein the weight ratio of the total amount of the compound of formula (I) to the total amount of further fragrance(s) and/or flavoring(s) is in the range of 1:1000 to 1:0.1, preferably 1:1000 to 1:0.5,
and
(b) Adding the fragrance and/or flavoring composition (a.1) or the compound/fragrances (a.2) to the article to be perfumed and/or flavored, in a sensory effective amount, preferably in an amount sufficient to impart, enhance and/or modify one or more scent and/or taste notes selected from the group consisting of the notes green, herbaceous, fresh, fruity, flowery, woody, animalic, sweet, earthy, ambry, greasy, metallic, balsamic, leather note and chlorine note, preferably one or more of the scent and/or taste notes selected from the group consisting of the notes green, woody, animalic, earthy, ambry, fruity, floral, leather note and chlorine note.

Furthermore, the present invention concerns a method for perfuming hair, skin, textile fibers, surfaces and/or room air comprising or consisting of the following steps:
(a) Providing
  (a.1) a fragrance and/or flavoring composition (as described herein), preferably containing a surfactant or a surfactant mixture,
  or
  (a.2) the compound of formula (I)

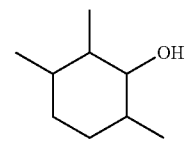

(I)

and optionally one, two, three, four, five, six, seven, eight, nine, ten or more further fragrance(s) and/or flavoring(s), wherein the weight ratio of the total amount of the compound of formula (I) to the total amount of further fragrance(s) and/or flavoring(s) is in the range of 1:1000 to 1:0.1, preferably 1:1000 to 1:0.5, and preferably additionally a surfactant or a surfactant mixture,
  or
  (a.3) an article according to the invention (as described herein), preferably containing a surfactant or surfactant mixture,
and
(b) Applying or incorporating the fragrance and/or flavoring composition (a.1) or the compound/fragrances (a.2) or the article (a.3) on the hair or skin or fibers or surface to be perfumed, or into the room air to be perfumed, in a sensory effective amount, preferably in an amount sufficient for the consumer to perceive one or more scent and/or taste notes selected from the group consisting of the notes green, herbaceous, fresh, fruity, flowery, woody, animal, sweet, earthy, ambry, greasy, metallic, balsamic and leather note, preferably at least one of the scent and/or taste notes selected from the group consisting of the notes green, woody, animal, earthy, ambry, fruity, floral and leather note.

Furthermore, preference is given to a method in accordance with the invention for perfuming hair, skin, textile fibers, surfaces and/or room air comprising or consisting of the following steps:

(a) Providing
  (a.1) a fragrance and/or flavoring composition (as described herein), preferably containing a surfactant or a surfactant mixture,
  or
  (a.2) the compound of formula (I)

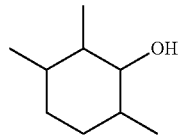

and optionally one, two, three, four, five, six, seven, eight, nine, ten or more further fragrance(s) and/or flavoring(s), wherein the weight ratio of the total amount of the compound of formula (I) to the total amount of further fragrance(s) and/or flavoring(s) is in the range of 1:1000 to 1:0.1, preferably 1:1000 to 1:0.5 and preferably additionally a surfactant or a surfactant mixture,
  or
  (a.3) an article according to the invention (as described herein), preferably containing a surfactant or surfactant mixture,
  and
(b) Applying or incorporating the fragrance and/or flavoring composition (a.1) or the compound/fragrances (a.2) or the article (a.3) on the hair or skin or fibers or surface to be perfumed, or into the room air to be perfumed, in a sensory effective amount, preferably in an amount sufficient for the consumer to perceive one or more scent and/or taste notes selected from the group consisting of the notes green, herbaceous, fresh, fruity, flowery, woody, animal, sweet, earthy, ambry, greasy, metallic, balsamic, leather note and chlorine note, preferably at least one of the scent and/or taste notes selected from the group consisting of the notes green, woody, animal, earthy, ambry, fruity, floral, leather note and chlorine note.

What is mentioned in connection with uses in accordance with the invention or fragrance and/or flavoring compositions in accordance with the invention or articles in accordance with the invention shall apply mutatis mutandis with respect to preferred embodiments of the methods described herein.

Furthermore, what is said in the context of one of the embodiments of the present invention described herein shall of course also apply to other embodiments described herein. Accordingly, the embodiments described herein can be combined with each other as desired—as far as this is reasonable for a person skilled in the art.

In the following, the invention is explained in more detail by means of examples. Unless otherwise stated, all values refer to the weight.

Abbreviations used: DPG=dipropylene glycol, TEC=triethyl citrate

EXAMPLE 1: PRODUCTION OF 2,3,6-TRIMETHYLCYCLOHEXANOL (COMPOUND OF FORMULA (I))

In a 250 ml autoclave, 138 g of 2,5,6-trimethylcyclohex-2-en-1-one in 50 g of isopropanol with 2 g of Raney nickel at 10 bar and 120° C. for 6 hours is hydrated. After cooling, the catalyst is filtered off and it is then concentrated. The raw product (141 g) is fractionally distilled in a 30 cm Vigreux column under vacuum.

Yield: 138 g (97.2% of theory)
Boiling point.: 95°-98° C./2 mbar
MS: m/z (%)=142(1-12), 124(20-57), 109(50-85), 95(56-98), 85(96-100), 71(62-100), 55(53-80), 41(48-77)

EXAMPLE 2: PERFUME COMPOSITION (FRAGRANCE COMPOSITION)

| IRIS SAFFIAN | |
|---|---:|
| Total in g (18 parts): | 1,000.00 |
| ALDEHYDE C14 SOG | 5 |
| ALLYLIONON | 4 |
| AMBROCENIDE ® 10 DPG 10% DPG | 10 |
| AMYRIS OIL | 100 |
| CEDAR WOOD OIL | 200 |
| ELEMI RESIN 70% IN BB | 275 |
| GUAJYLACETATE | 5 |
| IONON ALPHA | 80 |
| IRALDEIN GAMMA | 80 |
| IRISNITRILE 1% DPG | 25 |
| CARROT SEED OIL | 5 |
| MADRANOL ® | 100 |
| MYRRHEN ABSOLUE | 10 |
| NONADIENOL-2,6 1% DPG | 10 |
| PATCHOULI OIL DEGR. | 5 |
| PERUBALM OIL ED | 3 |
| TABANON 10% DPG | 3 |
| VERTOFIX | 80 |

According to the perfumers, the addition of 3% by weight of the compound of formula (I) (e.g. product of Example 1, 1% solution in DPG) makes this perfume composition more rounded and harmonious, adding a leather note and enhancing the woody and floral aspects. The combination or use according to the invention imparts an individual character to the composition and combines the different olfactory elements.

EXAMPLE 3: PERFUME COMPOSITION (FRAGRANCE COMPOSITION)

| CRISTAL CHEAP | |
|---|---:|
| Total in g (39 parts): | 1,000.00 |
| ALDEHYDE C14 SOG. | 3 |
| BASILIC OIL COMORES TYPE E | 0.5 |
| BENZYLSALICYLATE | 45 |
| CEDRYLACETATE | 5 |
| CITRAL FF | 2 |
| CITRONE RCO | 60 |
| CITRONELLOL 950 | 12 |
| CITRORANGE BASE COLIPA | 2 |
| DIHYDROJASMON | 4 |
| DIHYDROMYRCENOL | 10 |
| DIPROPYLEN GLYCOL | 201.5 |
| EVERNYL | 2 |
| FARENAL ® | 0.5 |
| GALBANUM OIL | 1 |
| GALBASCONE 10% DPG | 9 |
| GERANIOL SUPRA | 5 |
| GERANYLACETATE PUR | 3 |
| HEDION | 280 |
| HELIONAL | 25 |
| HERBAFLORAT | 5 |
| HEXYLCINNAMIC ALDEHYDE ALPHA | 45 |
| INDOLENE 50 RIZINUS OIL 10% DPG | 10 |
| ISORALDEIN 70 | 40 |

-continued

| CRISTAL CHEAP | |
|---|---|
| JASMIN 61 TYPE BASE | 10 |
| JASMOPYRAN | 4 |
| LAVENDER OIL MT. BLANC 40/42% | 2 |
| LILIAL | 35 |
| LINALOOL | 30 |
| LINALYLACETATE | 25 |
| MACROLIDE ® SUPRA | 3 |
| MYSORANE ® BASE | 20 |
| NEOFOLIONE 10% DPG | 2.5 |
| ORANGE OIL FLORIDA TYPE VALENZIA | 25 |
| PATCHOULI LIGHT | 2 |
| PHENYLETHYLALCOHOL | 20 |
| SANDRANOL ® | 5 |
| VETIVERYLIA BASE | 5 |
| YLANG MC TYPE BASE | 40 |
| ZIBETH AB0394E 10% DPG | 1 |

According to perfumers, this perfume composition is revived by the addition of 1% by weight of the compound of formula (I) (e.g. product of Example 1, 1% solution in DPG). The impression of fruitiness and floridity is considerably enhanced. The composition appears more harmonious, with a natural note added. The product from Example 1 (i.e. the isomer mixture of the compound of formula (I)) imparts its own character on the composition through its own odor and through its modifying and enhancing effect (booster effect) and combines the different olfactory elements.

EXAMPLE 4: PERFUME COMPOSITION (FRAGRANCE COMPOSITION)

| MAGIQUE | |
|---|---|
| Total in g (30 parts): | 1,000.00 |
| ALDEHYDE C14 SOG | 5 |
| AMBERWOOD ® F | 15 |
| AMBROCENIDE ® 10 DPG 10% DPG | 15 |
| BENZYLACETATE | 10 |
| BENZYLSALICYLATE | 95 |
| BERGAMOT IDENTOIL ® COLOURLESS | 25 |
| CASHMERAN | 5 |
| CEDAR WOOD OIL CHIN. | 20 |
| DAMASCONE DELTA 10% DPG | 10 |
| DIPROPYLEN GLYCOL | 195 |
| ELEMIOEL | 5 |
| ETHYLVANILLIN | 5 |
| FRAMBINON ® | 15 |
| GERANIOL 60 | 10 |
| GLOBALIDE ® | 120 |
| HEDION | 65 |
| HELIONAL | 10 |
| IONON BETA | 20 |
| ISO E SUPER | 95 |
| JASMIN ABS. BASE | 25 |
| LILIAL | 95 |
| METHYLBENZOAT 10% DPG | 5 |
| ORANGE OIL | 15 |
| PATCHOULI OIL GENUINE | 25 |
| PHENYLETHYLALCOHOL | 35 |
| ROSE OXIDE HIGH CIS 10% DPG | 5 |
| VANILLIN | 10 |
| YSAMBER ® K | 35 |
| ZIBETH AB0394E 10% DPG | 5 |
| CINNAMON ALCOHOL | 5 |

According to perfumers, the addition of 1% by weight of the compound of formula (I) (e.g. product from Example 1, 1% solution in DPG) to the perfume composition enhances its radiance. The impression of a fine leather note is considerably enhanced. The composition appears softer and a natural note is added. The product from Example 1 (i.e. the isomer mixture of the compound of formula (I)) imparts its own character on the composition through its own odor and through its modifying and enhancing effect (booster effect) and combines the different olfactory elements.

EXAMPLE 5: SHAMPOO

The product from Example 1 to be used according to the invention (i.e. the isomer mixture of the compound of formula (I)) was incorporated in a dosage of 0.5% by weight into a shampoo base of the following composition:

| | |
|---|---|
| Sodium lauryl ether sulphate (e.g. Texapon NSO, Cognis Deutschland GmbH) | 12% |
| Cocamidopropylbetaine (e.g. Dehyton K, Cognis Deutschland GmbH) | 2% |
| Sodium chloride | 1.4% |
| Citric acid | 1.3% |
| Phenoxyethanol, methyl, ethyl, butyl, and propyl paraben | 0.5% |
| Water | 82.8% |

The pH value of the shampoo base was about 6. From this, 100 mL of a 20 wt. % aqueous shampoo solution were prepared. In this shampoo solution, two hair strands were washed together for 2 minutes and then rinsed for 20 seconds under lukewarm running water. One hair strand was wrapped wet in aluminium foil and the second strand was dried with a hair dryer. Both hair strands were olfactorily assessed by a panel.

Olfactory description of both hair strands: Strongly woody, animal-like, earthy with an ambry note.

EXAMPLE 6: FABRIC SOFTENER

The perfume composition from Example 2 (after addition of 1% by weight of a 1% solution of the product from Example 1 in DPG) was incorporated in a dosage of 0.5% by weight into a fabric softener base having the following composition:

| | |
|---|---|
| Quaternary ammonium methosulphate (esterquat), approx. 90% (e.g. Rewoquat WE 18, Witco Surfactants GmbH) | 5.5% |
| Alkyldimethylbenzylammonium chloride, approx. 50% (e.g. Preventol R50, Bayer AG) | 0.2% |
| Ink solution, approx. 1% | 0.3% |
| Water | 94.0% |

The pH value of the fabric softener base was in the range of 2 to 3. Two fabric cloths were rinsed with 370 g of a 1% aqueous fabric softener solution based on 0.5% by weight of the perfume composition from Example 2 comprising the fabric softener base in a linetest machine at 20° C. for 30 minutes in the fabric softening program. The cloths were wrung out and then spun for 20 seconds. One cloth was welded in wet and one was hung up to dry. Afterwards, both cloths were olfactorily assessed by a panel.

Olfactory description of both fabric cloths: Rounded and harmonious in smell, with a fine leather note.

EXAMPLE 7: POWDER LAUNDRY DETERGENT

The perfume oil composition from Example 3 (after addition of 1% by weight of a 1% solution of the product from Example 1 in DPG) was incorporated in a dosage of 0.4% by weight into a laundry detergent base having the following formulation:

| | |
|---|---|
| Linear sodium alkylbenzenesulfonate | 8.8% |
| Ethoxylated fatty alcohol C12-18 (7 EO) | 4.7% |
| Sodium soap | 3.2% |
| Defoamer DOW CORNING 2-4248S POWDERED ANTIFOAM, ilicone oil on zeolite as carrier material | 3.9% |
| Zeolite 4A | 28.3% |
| Sodium carbonate | 11.6% |
| Sodium salt of an acrylic copolymer and maleic acid (Sokalan CP5) | 2.4% |
| Sodium Silicate | 3.0% |
| Carboxymethyl cellulose | 1.2% |
| Dequest 2066 ([[(phosphonomethyl)imino]bis[(ethylenenitrilo)bis(methylene)]]tetrakis-phosphonic acid, sodium salt) | 2.8% |
| Optical brightener | 0.2% |
| Sodium sulfate | 6.5% |
| Protease | 0.4% |
| Sodium perborate tetrahydrate | 22.0% |
| TAED | 1.0% |

Two fabric cloths were washed with 370 g of a 1% aqueous laundry detergent solution based on 0.4% by weight of the perfume oil composition from Example 3 comprising the laundry detergent base (the pH value of the laundry detergent solution is clearly in the basic range) for 45 minutes at 60° C. in a line test machine in the main wash cycle. The cloths were first rinsed with cold water for 5 minutes, wrung out and then spun for 20 seconds. One cloth was welded in wet and one was hung up to dry. Afterwards both cloths were olfactorily evaluated by a panel.

Olfactory description of both fabric cloths: Fruity and flowery, harmonious, with a natural woody note.

EXAMPLE 8: TOOTHPASTE

Toothbrush composition comprising a fragrance and flavoring composition having a wintergreen character

EXAMPLE 8.1: COMPARATIVE EXAMPLE

By mixing of

| | | |
|---|---|---|
| 17 | Weight % | peppermint oil *Mentha arvensis*, rectified |
| 17.5 | Weight % | peppermint oil *Mentha piperita* type Willamette |
| 25 | Weight % | methyl salicylate |
| 40 | Weight % | l-menthol |
| 0.5 | Weight % | menthanecarboxylic acid-N-(4-methoxyphenyl)-amide | a fragrance and flavoring composition for toothbrush compositions with wintergreen character was produced.

EXAMPLE 8.2

By mixing of

| | | |
|---|---|---|
| 17 | Weight % | Peppermint oil *Mentha arvensis*, rectified |
| 17.5 | Weight % | Peppermint oil *Mentha piperita* type Willamette |
| 25 | Weight % | methyl salicylate |
| 40 | Weight % | l-menthol |
| 0.3 | Weight % | Menthanecarboxylic acid-N-(4-methoxyphenyl)-amide |
| 0.2 | Weight % | Product of example 1 (compound of formula (I)) | a fragrance and flavoring composition according to the invention was prepared containing 0.2% by weight of the compound of formula (I) for toothbrush compositions having a wintergreen character.

The fragrance and flavoring compositions according to Example 8.1 (for a comparative toothbrush composition) and Example 8.2 (for a toothbrush composition according to the invention) were each incorporated at a concentration of 1.2% by weight into a respective standard silica-based toothpaste composition based on the total mass of the resulting toothpaste.

The resulting toothpastes were tested under practical conditions by an expert panel trained in sensory analysis. The sensory evaluation for the toothpaste containing a fragrance and flavoring composition according to example 8.2 resulted in a distinct fresh peppermint wintergreen note with a very strong and pronounced, very long-lastingcooling freshness sensation and a slight chlorine note, which conveys an antibacterial effectiveness of the toothpaste. The chlorine note was not perceptible in the comparative toothbrush composition 8.1.

EXAMPLE 9: MOUTHWASH

Mouthwash or mouthwash concentrate comprising a fragrance and flavoring composition having eucalyptus character

EXAMPLE 9.1: COMPARATIVE EXAMPLE

By mixing of

| | | |
|---|---|---|
| 10 | Weight % | Anethole |
| 17.5 | Weight % | Eucalyptus oil (70-75% 1,8-cineol) |
| 17.5 | Weight % | 1,8-cineol (Eucalyptol) |
| 54.4 | Weight % | l-menthol |
| 0.6 | Weight % | Menthanecarboxylic acid-N-(4-methoxyphenyl)-amide | a fragrance and flavoring composition was produced for use in mouthwashes and mouthwash concentrates.

EXAMPLE 9.2

By mixing of

| | | |
|---|---|---|
| 10 | Weight % | Anethole |
| 17.5 | Weight % | Eucalyptus oil (70-75% 1,8-cineol) |
| 17.5 | Weight % | 1,8-cineol (Eucalyptol) |
| 54.4 | Weight % | l-menthol |
| 0.3 | Weight % | Menthanecarboxylic acid-N-(4-methoxyphenyl)-amide |
| 0.3 | Weight % | Product from example 1 (compound of formula (I)) | a fragrance and flavoring composition was prepared containing 0.2% by weight of the compound of formula (I) for use in mouthwash and mouthwash concentrates.

The fragrance and flavoring compositions according to Example 9.1 (for a comparative mouthwash or mouthwash concentrate) and Example 9.2 (for a mouthwash or mouthwash concentrate according to the invention) were each incorporated with a concentration of 0.45% by weight into a ready-to-use mouthwash or each with a concentration of 3% by weight into a ready-to-use mouthwash concentrate, based on the total mass of the resulting mouthwash or the resulting mouthwash concentrate.

The resulting mouthwash and mouthwash concentrates were tested under practical conditions by a sensory trained expert panel. The sensory evaluation for the mouthwash/mouthwash concentrate, containing a fragrance and flavoring composition according to Example 9.2, resulted in a strong, pleasantly fresh eucalyptus note with a very long-lasting freshness sensation, which persisted even after the mouthwash/mouthwash concentrate had been used for well over 30 minutes. In addition, a chlorine note can be clearly perceived, which conveys an impression of hygiene and antibacterial effectiveness. In contrast, the mouthwash/mouthwash concentrate containing a fragrance and flavoring composition according to Example 9.1 does not have a perceptible chlorine note.

EXAMPLE 10: ALL-PURPOSE CLEANER

| Material | Manufacturer | Chemical Name | Function | Wt.-% |
|---|---|---|---|---|
| Deionized water | | Water | Solvent | 59.6 |
| Mergal K9N | Troy Chemie, Seelze | 5-Chloro-2-methyl-3-(2H)-isothiazolone and 2-methyl-3-(2H)-isothiazolone | Preservative | 0.1 |
| Tri Sodium Citrate Dihydrate | Various | Tri Sodium Citrate Dihydrate | Complexing agent | 3.0 |
| Zetesol NL-2 | Zschimmer & Schwarz, Germany | Fatty alcohol C12-14-sulfate, Sodium | Anionic surfactant | 30.0 |
| Imbentin C/125/055 | Dr. W. Kolb AG Chem. | Fatty alcohol C12-C15, 8EO | Nonionic detergent surfactant | 5.0 |
| Ethanol 96% | Various | Ethanol | Solvent | 2.0 |
| Perfume composition from Example 3 | Symrise | | Perfume (Fragrance) | 0.3 |

At a dosage of 0.3% by weight of the perfume composition from Example 3 in the all-purpose cleaner, the following results are obtained:

Adding 1% by weight of a 1% solution of the product from Example 1 in DPG (based on the total weight of the perfume composition from Example 3) to the all-purpose cleaner significantly enhances the impression of fruitiness and floridity. In addition, after the addition of the compound of formula (I), a discreet chloroskatol note can be perceived which conveys the impression of cleanliness and hygiene

The invention claimed is:

1. A fragrance and/or flavoring composition comprising:
  (a) a compound of formula (I), and

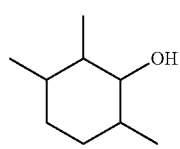

(I)

(b) one or more further fragrance(s) and/or flavoring(s), wherein the weight ratio of the total amount of the compound of formula (I) to the total amount of the one or more further fragrance(s) and/or flavoring(s) is 1:1000 to 1:0.1.

2. The fragrance and/or flavoring composition according to claim 1, wherein the total amount of the compound of formula (I) is 0.0001 to 99.9% by weight, based on the total weight of the fragrance and/or flavoring composition.

3. The fragrance and/or flavoring composition according to claim 1, wherein the amount of the compound of formula (I) in the composition is sufficient to impart and/or enhance one or more scent and/or flavor notes selected from green, herbaceous, fresh, fruity, flowery, woody, animal, sweet, earthy, ambry, greasy, metallic, balsamic, leather, and chlorine.

4. The fragrance and/or flavoring composition according to claim 1, wherein the one or more further fragrance(s) and/or flavoring(s) impart, modify, and/or enhance one or more scent and/or flavor notes selected from green, herbaceous, fresh, fruity, floral, woody, animalic, sweet, earthy, ambry, greasy, metallic, balsamic, leather, and chlorine.

5. A perfumed and/or flavored article comprising:
  (i) the fragrance and/or flavoring composition of claim 1; and
  (ii) one or more additive(s), excipient(s), and/or active substance(s).

6. The perfumed and/or flavored article according to claim 5, wherein the article is selected from laundry detergents, cleaning products, hygiene products, and personal care products.

7. The perfumed and/or flavored article of claim 5, wherein the article is selected from a surface cleaner, a bathroom cleaner, an all-purpose cleaner, a mouthwash, a toothpaste, a tooth gel, a tooth powder, a tooth care chewing gum, a perfume extract, a perfume, a toiletry, a shaving lotion, a cologne, a pre-shave product, a splash cologne, a perfumed refreshing wipe, an acidic, alkaline or neutral detergent, a textile freshener, an ironing aid, a liquid laundry detergent, a powdery laundry detergent, a laundry pretreatment agent, a fabric softener, a washing soap, a washing tablet, a disinfectant, a surface disinfectant, an air freshener, an aerosol spray, a wax or polish, a body care product, a hand cream, a lotion, a foot cream, a foot lotion, a depilatory cream, a depilatory lotion, an after-shave cream, an after-shave lotion, a tanning cream, a tanning lotion, a hair care product, a deodorant, an antiperspirant, a decorative cosmetic product, a candle, a lamp oil, an incense stick, an insecticide, a repellent, and a fuel.

8. The perfumed and/or flavored article of claim 5, wherein the amount of (i) in the article is sufficient for a consumer to perceive one or more scent and/or flavor notes selected from green, herbaceous, fresh, fruity, flowery, woody, animal, sweet, earthy, ambry, greasy, metallic, balsamic, leather, and chlorine.

9. The perfumed and/or flavored article according to claim 5, wherein the total amount of the compound of formula (I) is 0.00001 to 10% by weight, based on the total weight of the article.

10. The perfumed and/or flavored article according to claim 5, wherein the total amount of the compound of formula (I) is 0.001 to 2% by weight, based on the total weight of the article.

11. The perfumed and/or flavored article according to claim 5, wherein the total amount of the compound of formula (I) is 0.005 to 1% by weight, based on the total weight of the article.

12. The fragrance and/or flavoring composition of claim 1, wherein the one or more further fragrance(s) and/or flavoring(s) imparts one or more scent(s) and/or flavor notes selected from green, herbaceous, fresh, fruity, floral, woody, animalic, sweet, earthy, ambry, greasy, metallic, balsamic, leather, and chlorine.

13. A method for perfuming and/or flavoring an article comprising combining a sensorially effective amount of a fragrance and/or flavoring composition according to claim 1 with an article.

14. A method for perfuming hair, skin, textile fibers, a surface, and/or room air comprising contacting the hair, skin, textile fibers, surface, and/or room air with a sensorially effective amount of the fragrance composition according to claim 1.

15. A method for perfuming and/or flavoring a composition comprising incorporating a compound formula (I)

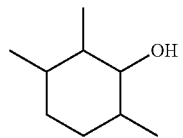
(I)

and one or more further fragrance(s) and/or flavoring(s) into the composition in amount sufficient to perfume and/or flavor the composition, wherein the weight ratio of the total amount of the compound of formula (I) to the total amount of the one or more further fragrance(s) and/or flavoring(s) is 1:1000 to 1:0.1.

16. The method of claim 15, wherein the one or more further fragrance(s) and/or flavoring(s) provides one or more scent(s) and/or flavor notes selected from green, herbaceous, fresh, fruity, floral, woody, animalic, sweet, earthy, ambry, greasy, metallic, balsamic, leather, and chlorine.

17. The method of claim 16, wherein the weight ratio of the total amount of the compound of formula (I) to the total amount of the one or more further fragrance(s) and/or flavoring(s) in the composition is 1:1000 to 1:0.5.

18. The method of claim 15, wherein the compound of formula (I) is in an amount sufficient to impart, modify, and/or enhance one or more scent(s) and/or flavor notes selected from green, woody, animal, earthy, ambry, fruity, floral, leather note and chlorine note.

* * * * *